United States Patent [19]

Fernandez

[11] Patent Number: 4,898,732
[45] Date of Patent: Feb. 6, 1990

[54] INHIBITING OF TUMOR GROWTH WITH AN ANTAGONIST OF THE RENIN-ANGIOTEN-SIN SYSTEM

[75] Inventor: Leonardo A. Fernandez, Guilford, Conn.

[73] Assignee: The Clinipad Corporation, Guilford, Conn.

[21] Appl. No.: 190,158

[22] Filed: May 4, 1988

[51] Int. Cl.$^4$ ............................................. A61F 13/00
[52] U.S. Cl. ................................... 424/422; 424/423; 424/426
[58] Field of Search ..................... 514/16, 17; 424/427, 424/428

[56] References Cited

U.S. PATENT DOCUMENTS 3,932,624  1/1976  Fulton .................................... 514/16
4,416,595  11/1983  Cromie ................................. 417/476

OTHER PUBLICATIONS

Dominic Bazuck et al., Diagnosis and Treatment of Renin-Secreting Tumors, etc., vol. 6, No. 5, Sep.-Oct. 1984, pp. 760-766.
Product Information concerning enalapril maleate, pp. 1406 & 1407.
Product Information concerning captopril, pp. 2046-2048.
Diagnostic Product Information concerning saralasin acetate, pp. 3011-3013.
Leonardo A. Fernandez et al., Renin-angiotensin and Development of Collateral Circulation after Renal Ischemia; American Journal of Physiology, vol. 243, pp. H869-H875, (1982).
Jane L. Frederick, M.D. et al., Initiation of Angiogenesis by Porcine Follicular Fluid, American Journal of Obstet Gynecol, Aug. 15, 1985, vol. 152, No. 8, pp. 1073-1078.
Fernandez et al., Angiotensin II Decreases Mortality Rate in Gerbils with Unilateral Carotid Ligation, Stroke vol. 17, No. 1, Jan.-Feb., 1986, pp. 82-85.
Fernandez et al., Renin in Angiolymphoid Hyperplasia with Eosinophilia Arch. Pathol. Lab. Med., vol. 110, Dec., 1986, pp. 1131-1135.
Fernandez et al., Neovascularization Produced by Angiotensin II, The Journal of Laboratory and Clinical Medicine, vol. 105, No. 2, pp. 141-145, Feb., 1985.
Dominique Baruch et al., Diagnosis and Treatment of Renin-Secreting Tumors, Report of Three Cases, Hypertension Case Reports, vol. 6, No. 5, Sep.-Oct., 1984, pp. 760-766.
Michael J. Peach, Renin-Angiotensin System: Biochemistry and Mechanisms of Action, Physiological Reviews, vol. 57, No. 2, Apr., 1977, pp. 313-370.
John B. Kostis et al., Angiotensin Converting Enzyme Inhibitors, Alan R. Liss, Inc., New York, pp. 213-261, (1987).

Primary Examiner—Thurman K. Page
Assistant Examiner—Leon R. Horne
Attorney, Agent, or Firm—Garrettson Ellis

[57] ABSTRACT

A method of inhibiting tumor growth in a patient which comprises administering to the patient an effective dose of a pharmaceutical antagonist of the renin-angiotensin system of the patient.

7 Claims, 1 Drawing Sheet

INHIBITING OF TUMOR GROWTH WITH AN ANTAGONIST OF THE RENIN-ANGIOTEN-SIN SYSTEM

BACKGROUND OF THE INVENTION

In the article by Leonardo A. Fernandez et al. entitled Renin-Angiotensin and Development of collateral Circulation After Renal Ischemia, Am.J. Physiol. 243 (Hart, Circ. Physiol. 12) H869-H875, 1982, it is reported that the infusion of angiotensin-II to aortic-ligated left renoprival animals tends to restore blood flow to muscle. From this, the article concludes that after renal ischemia, the renin-angiotensin system, independent of its hypertensive effect, restores blood flow by stimulating the development of collateral circulation.

The resin-angiotensin system is a well-known biochemical pathway in mammals, which is best known for its effect on blood pressure. The renin-angiotensin system also governs the concentration of plasma aldosterone, through which intermediate the potent action of angiotensin II may be effected. However, the exact mechanism of angiotensin II is not known, and the invention of this application is not intended to be limited to any particular theory about mechanisms of operation.

Angiotensin II has been planted into avascular rabbit cornea, and it has been demonstrated that this substance strongly promotes local new blood vessel formation; Fernandez, L. A. et al. Neovascularization Produced by Angiotensin II, J. Lab. Clin. Med. 1985; 105:141-145; Meade Twickler & Fernandez: Neovascularization Produced by Angiotensin II. Fed. Proc. 1982; 41: 12-1230.

It is known that tumors have a capability of inducing the growth of surrounding vascular system to provide the tumor with an adequate supply of blood. In those events where a supporting vascular system does not grow, the size of the tumor is limited by the lack of a supporting blood system.

It has been found that angiotensin II is a very potent angiogenic factor. It can elicit blood vessel growth in the rat cornea when present at extremely low concentrations.

DESCRIPTION OF THE INVENTION

The invention of this application relates to a method of inhibiting tumor growth in a patient which carries at least one tumor, which comprises administering to the patient an effective dose of a pharmaceutical antagonist of the renin-angiotensin system of the patient. Some tumors stimulate the growth of a supporting vascular system by the manufacture of renin, which is then processed through the renin-angiotensin system, with the result that a supporting vascular system grows about the tumor. In accordance with this invention, it has been discovered that such tumors may have their growth inhibited by inhibition of the growth of the supporting vascular system for the tumor by the use of an antagonist for the renin-angiotensin system of the patient.

The patient is desirably a human patient, but the invention is effective with respect to animals such as the rat, which are intended to be included in the term "patient".

Pharmaceutical antagonists for the renin-angiotensin system are well-known. Specific pharmaceutical antagonists which are currently available for use as drugs include saralasin acetate, sold under the trademark SARENIN by Norwich-Eaton Pharmaceuticals; captopril (sold under the trademark CAPTOTEN by Squibb); and enalapril maleate (sold under the trademark VASOTEC by Merck, Sharp, and Dohme). According to published literature, enalapril maleate and captopril are indicated for use in the treatment of hypertension. Both of the drugs are stated to act by suppressing the conversion of angiotensin I to the vasoconstrictor substance, angiotensin II.

Saralasin acetate is indicated for use as a diagnostic agent for the detection of angiotensin II-dependent hypertension, and is stated to act as an angiotensin II analog that binds to angiotensin II receptors, but is a less effective vasoconstrictive agonist than angiotensin II. Thus, saralasin acetate acts as an antagonist of angiotensin II, lowering blood pressure. However, in the presence of low levels of circulating angiotensin II, saralasin acetate can behave as an agonist, raising the blood pressure.

Others of such pharmaceutical antagonists may also be used in accordance with this invention; for example the angiotensin converting enzyme inhibitors listed and discussed in the publication of John B. Kostis, M.D., et al entitled Angiotensin Converting Enzyme Inhibitors, published by Alan R. Liss, Inc. of New York, specifically Alecepril, Cilazapril, Delapril, Fentiapril, Fosenopril, Lisinopril, Pentopril, Perindopril, Pivalopril, Quinapril, Ramipril, Spirapril, Zofenopril, etc..

The pharmaceutical antagonists of this invention may be administered to a patient in any conventional manner including orally, intravenously, by regional perfusion of an isolated appendage or organ by direct administration through a medical pump directly to the tumor site (see for example U.S. Pat. No. 4,416,595), or the like. Particularly, one may implant in a patient a controlled release member of any known type, the member containing and releasing in a controlled manner an effective dose of a pharmaceutical antagonist of the renin-angiotensin system of the patient. The controlled release member may be implanted at a tumor site, thus causing the slow release of the pharmaceutical antagonist for continuing inhibition of the growth of vascularization in the patient at least in an area adjacent the implanted controlled-release member.

A large number of controlled release members are well known and described in the patent literature and elsewhere, and there is no intrinsic limitation against the use of the invention of this application in conjunction with any of them. Particularly, the pharmaceutical antagonist of this invention may be dispersed into a controlled release member such as a small mass of silicone rubber or a hydroxylated acrylate compound which is well known for use in contact with living cells, for example the material sold as HYDRON plastic, or the like.

The respective dosages of the pharmaceutical antagonists used in this invention are typically the specific recommended dosages in current use with respect to the specific embodiments of pharmaceutical antagonists listed above. The usual dosage ranges for human beings for these drugs are as follows:

for enalapril maleate 10–40 mg. per day administered in a single dose or two divided doses;

for captopril, 25–50 mg. bid. or tid. but if necessary, up to a maximum daily dose of 450 mg;

for saralasin acetate, from 0.05 to 20 micrograms/kg./min.

The published literature on these drugs should be consulted, and the warnings about side effects and the like should be carefully considered as these materials are used.

The above dosages are of course for a whole body treatment in accordance with this invention. If regional perfusion of a single organ or appendage is being used, the dosage should, of course, be appropriately adjusted. Regional perfusion is any procedure in which attempts are made to provide a more concentrated amount of the pharmaceutical antagonist used in a specific area of the body while minimizing the concentration in other areas of the body. This may be done by closing off or restricting blood flow to an arm or leg, for example, and recirculating oxygenated blood through such appendage with a high concentration of the pharmaceutical antagonist used therein, so that the entire body is spared the high load of pharmaceutical antagonist. Additionally, one may place the pharmaceutical antagonist by a catheter and optionally a mechanical pump directly into the tumor site, for example, or directly into an affected organ, to increase the concentration of pharmaceutical antagonist at the desired site over the overall concentration in the body.

It is believed that the above three specific examples of pharmaceutical antagonists of renin-angiotensin system are not the only materials that can be expected to be effective in accordance with this invention. It is contemplated that equivalent materials will be available, and can be expected to be operative if their action is to suppress the amount or effect of angiotensin II provided to a tumor site, to inhibit vascularization of the tumor.

DESCRIPTION OF THE SPECIFIC EMBODIMENT

Figure 1:
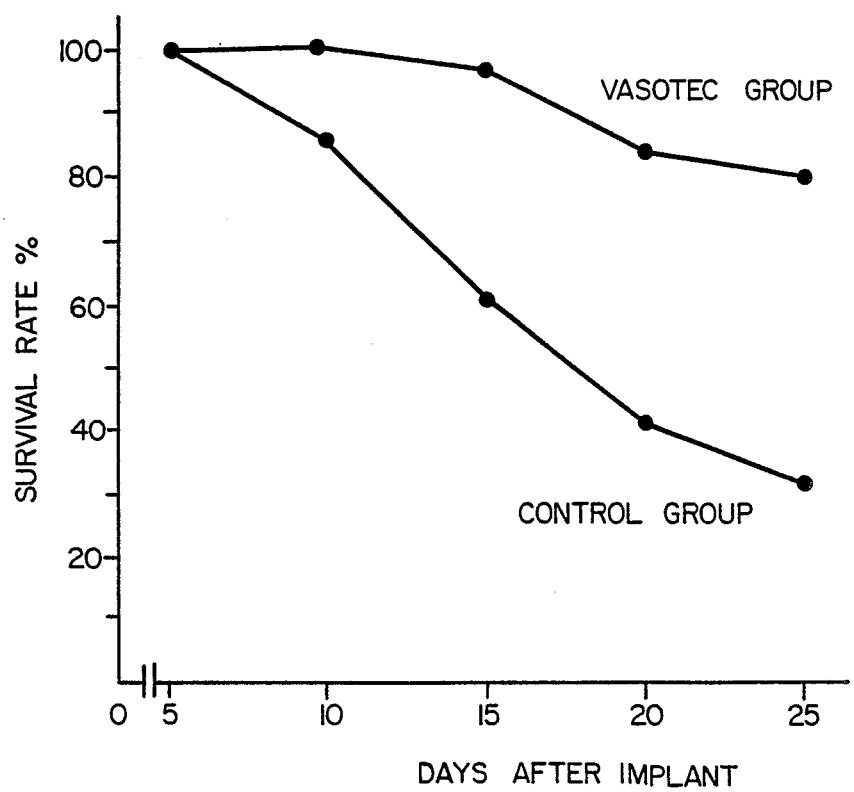
FIG. 1 is a graph showing the survival rate of tumor-carrying rats which have been treated in accordance with this invention, compared with a control group.

The disclosure above, and the examples below, are offered for illustrative purposes only, and are not intended to limit the scope of the invention of this application, which is as defined in the claims below.

EXAMPLE I

FIG. 1 shows the result of an experiment with 60 rats which were implanted with a Walker 256 carcinosarcoma rat tumor in the flank of each rat.

Thereafter, 30 of the rats in a control group were provided with normal maintenance, while the remaining 30 rats were identically maintained, but with one mg/ml of Vasotec (brand of enalapril maleate) dissolved in their drinking water.

FIG. 1 shows the survival rate expressed as a percentage of each group of rats over a period of 25 days. It can be seen that mortality in the group of rats receiving Vasotec was very significantly inhibited, in that at the end of the 25 days, about 80 percent of the Vasotec rats had survived, compared with only 30 percent of the control group rats.

Although tumor size was not measured in this experiment, post mortem examination showed that gross necrosis of the tumor in Vasotec-treated animals appeared larger than in the control group.

EXAMPLE II

Rats were anesthetized, and a pocket was made in the stroma of cornea of their eyes. Into each surgically prepared pocket was added a bead of Hydron brand hydroxylated acrylate plastic which contained an extract from a human brain tumor (glioblastroma multiforme). The extract was incorporated into Hydron plastic dissolved in solution, with a known amount of said solution pipetted into Teflon plastic molds and allowed to dry overnight at 4 degrees C. to form a solid bead. Some of the beads formed in this manner were formulated to also contain 50 micrograms of saralasin acetate per bead.

The plastic bead was surgically installed in the rat cornea, to release in a slow, controlled manner elements of the tumor extract, and saralasin acetate, when present.

Eleven rat eyes were implanted with a Hydron plastic bead which contained saralasin acetate. Ten control rats eyes were treated with the plastic beads which contained glioblastroma multiforme extract but which was free of saralasin acetate.

After 6 days, the rats were sacrificed and their eyes dissected. The control group of rats (glioblastroma multiforme extract alone) was found to have an average of 33.0 blood vessels present in the cornea, the cornea being normally free of blood vessels. Those rats which carried the plastic bead containing glioblastroma multiforme extract plus saralasin acetate had an average of 5.3 blood vessels in the cornea. This tends to indicate that the human brain tumor extract carries a factor that strongly encourages vascularization. At the same time, the data also shows that the continuing presence of a pharmaceutical antagonist of the renin-angiotensin system, and particularly saralasin acetate, can suppress the growth of vascularization.

Additionally, the same rat eyes were examined for the degree of penetration of the blood vessels into the cornea in accordance with the method described in the article by Jane L. Frederick, et al. entitled Initiation of Angiogenesis by Porcine Follicular Fluid, Am. J. Obstet. Gynecol. 1985: Vol. 152, pp. 1073–1078. On the basis of arbitrary score as described by that article, the control group rats exhibited a blood vessel penetration score of 2.9, while the rat eyes which carried saralasin acetate exhibited a lesser blood vessel penetration score of 2.3, providing further indication of the inhibitory effect of vascularization, in accordance with this invention.

That which is claimed is:

1. The method of implanting in a patient a controlled-release member, said member containing and releasing in controlled manner an effective dose a member selected from the group consisting of enalapril maleate, catapril and seralasin acetate, of a pharmaceutical antagonist of the renin-angiotensin system of said patient, whereby the growth of vascularization in said patient at least in an area adjacent said implanted controlled-release member is inhibited.

2. The method of claim 1, in which said controlled-release member is implanted at a tumor site.

3. The method of claim 2 in which said pharmaceutical antagonist is saralasin acetate.

4. The method of claim 2 in which said pharmaceutical antagonist is an antagonist to the action of angiotensin II.

5. The method of claim 2 in which said pharmaceutical antagonist inhibits the conversion of angiotensin I to angiotensin II.

6. The method or claim 2 in which said pharmaceutical antagonist is enalapril maleate.

7. The method of claim 2 in which said pharmaceutical antagonist is captopril.

* * * * *